US007433484B2

(12) United States Patent
Asseily et al.

(10) Patent No.: US 7,433,484 B2
(45) Date of Patent: Oct. 7, 2008

(54) ACOUSTIC VIBRATION SENSOR

(75) Inventors: Alexander Asseily, San Francisco, CA (US); Andrew E. Einaudi, San Francisco, CA (US)

(73) Assignee: AliphCom, Inc., San Francisco, CA (US)

( * ) Notice: Subject to any disclaimer, the term of this patent is extended or adjusted under 35 U.S.C. 154(b) by 542 days.

(21) Appl. No.: 10/769,302

(22) Filed: Jan. 30, 2004

(65) Prior Publication Data

US 2004/0249633 A1 Dec. 9, 2004

Related U.S. Application Data

(60) Provisional application No. 60/443,818, filed on Jan. 30, 2003.

(51) Int. Cl.

*H04R 1/20* (2006.01)
*H04R 1/02* (2006.01)
*H04R 25/00* (2006.01)
*A61F 11/06* (2006.01)
*G10K 11/16* (2006.01)
*H03B 29/00* (2006.01)

(52) U.S. Cl. ....................... 381/355; 381/322; 381/326; 381/71.2; 381/345; 381/357

(58) Field of Classification Search ................. 381/151, 381/173, 372, 345–348, 354, 162, 355–357, 381/359, 361, 364, 366, 367, 368, 112–117, 381/314, 322, 324, 326, 331, 71.2

See application file for complete search history.

(56) References Cited

U.S. PATENT DOCUMENTS 3,789,166 A 1/1974 Sebesta
4,006,318 A 2/1977 Sebesta et al.
4,591,668 A 5/1986 Iwata (Continued)

FOREIGN PATENT DOCUMENTS

EP 0 637 187 A 2/1995

(Continued)

OTHER PUBLICATIONS

Gregory C. Burnett: "The Physiological Basis of Glottal Electromagnetic Micropower Sensors (GEMS) and Their Use in Defining an Excitation Function for the Human Vocal Tract" Dissertaton University of California at Davis Jan. 1999 USA.

(Continued)

*Primary Examiner*—Wayne Young
*Assistant Examiner*—Dionne H Pendleton
(74) *Attorney, Agent, or Firm*—Courtney Staniford & Gregory LLP

(57) ABSTRACT

An acoustic vibration sensor, also referred to as a speech sensing device, is provided. The acoustic vibration sensor receives speech signals of a human talker and, in response, generates electrical signals representative of human speech. The acoustic vibration sensor includes at least one diaphragm positioned adjacent to a front port and at least one coupler. The coupler couples a first set of signals to the diaphragm while isolating the diaphragm from the second set of signals. The coupler includes at least one material with acoustic impedance matched to the acoustic impedance of human skin.

17 Claims, 7 Drawing Sheets

U.S. PATENT DOCUMENTS

| | | | | | |
|---|---|---|---|---|---|
| 4,607,383 | A | * | 8/1986 | Ingalls | 381/113 |
| 4,901,354 | A | | 2/1990 | Gollmar et al. | |
| 4,949,387 | A | * | 8/1990 | Andert et al. | 381/190 |
| 5,097,515 | A | | 3/1992 | Baba | |
| 5,150,418 | A | * | 9/1992 | Honda et al. | 381/349 |
| 5,212,764 | A | | 5/1993 | Ariyoshi | |
| 5,400,409 | A | | 3/1995 | Linhard | |
| 5,406,622 | A | | 4/1995 | Silverberg et al. | |
| 5,414,776 | A | | 5/1995 | Sims, Jr. | |
| 5,473,702 | A | | 12/1995 | Yoshida et al. | |
| 5,515,865 | A | | 5/1996 | Scanlon | |
| 5,517,435 | A | | 5/1996 | Sugiyama | |
| 5,539,859 | A | | 7/1996 | Robbe et al. | |
| 5,633,935 | A | | 5/1997 | Kanamori et al. | |
| 5,649,055 | A | | 7/1997 | Gupta et al. | |
| 5,684,460 | A | | 11/1997 | Scanlon | |
| 5,729,694 | A | | 3/1998 | Holzrichter et al. | |
| 5,754,665 | A | | 5/1998 | Hosoi et al. | |
| 5,790,684 | A | * | 8/1998 | Niino et al. | 381/326 |
| 5,835,608 | A | | 11/1998 | Warnaka et al. | |
| 5,853,005 | A | | 12/1998 | Scanlon | |
| 5,917,921 | A | | 6/1999 | Sasaki et al. | |
| 5,966,090 | A | | 10/1999 | McEwan | |
| 5,986,600 | A | | 11/1999 | McEwan | |
| 6,006,175 | A | | 12/1999 | Holzrichter | |
| 6,009,396 | A | | 12/1999 | Nagata | |
| 6,069,963 | A | | 5/2000 | Martin et al. | |
| 6,188,773 | B1 | * | 2/2001 | Murata et al. | 381/361 |
| 6,191,724 | B1 | | 2/2001 | McEwan | |
| 6,266,422 | B1 | | 7/2001 | Ikeda | |
| 6,430,295 | B1 | | 8/2002 | Handel et al. | |
| 6,685,638 | B1 | * | 2/2004 | Taylor et al. | 600/437 |
| 6,771,788 | B1 | * | 8/2004 | Soutar et al. | 381/355 |
| 2002/0039425 | A1 | | 4/2002 | Burnett et al. | |

FOREIGN PATENT DOCUMENTS

| | | | |
|---|---|---|---|
| EP | 0 795 851 | A2 | 9/1997 |
| EP | 0 984 660 | A2 | 3/2000 |
| JP | 2000 312 395 | | 11/2000 |
| JP | 2001 189 987 | | 7/2001 |
| WO | WO 02 07151 | | 1/2002 |

OTHER PUBLICATIONS

L.C. Ng et al.: Speaker Verification Using Combined Acoustic and EM Sensor Signal.

A. Hussain: "Intelligibility Assessment of a Multi-Band Speech Enhancement Scheme", Proceedings IEEE.

Zhao Li et al: "Robust Speech Coding Using Microphone Arrays", Signals Systems and Computers, 1997.

L.C. Ng et al.: "Denoising of Human Speech Using Combined Acoustic and EM Sensor Signal Processing".

S. Affes et al.: "A Signal Subspace Tracking Algorithm for Microphone Array Processing of Speech". I.

* cited by examiner

Section A-A

Section A-A

ACOUSTIC VIBRATION SENSOR

RELATED APPLICATION

This application claims priority to U.S. patent application No. 60/443,818, filed Jan. 30, 2003. This application relates to the following U.S. patent application Ser. Nos. 09/990,847 filed Nov. 21, 2001; 10/159,770, filed May 30, 2002; 10/301,237, filed Nov. 21, 2002; 10/383,162, filed Mar. 5, 2003; 10/400,282, filed Mar. 27, 2003; and 10/667,207, filed Sep. 18, 2003.

TECHNICAL FIELD

The present invention relates to devices for sensing acoustic vibrations.

BACKGROUND

A number of devices are typically used in communications devices such as handsets (mobile and wired telephones) and headsets (all types) for example, to detect the speech of a user. These devices include acoustic microphones, physiological microphones, and accelerometers.

One common device typically used for detecting speech is an acoustic pressure sensor or microphone. One example of an acoustic pressure sensor is an electret condenser microphone, which can currently be found in numerous mobile communication devices. These electret condenser microphones have been miniaturized to fit into mobile devices such as cellular telephones and headsets. A typical device might have a diameter of 6 millimeters (mm) and a height of 3 mm. The problem with these electret condenser microphones is that because the microphones are designed to detect acoustic vibrations in the air, they generally detect ambient acoustic noise in addition to the speech signal of interest. The received speech signal therefore often includes noise (such as engines, people, and wind), much of which cannot be removed without degrading the speech quality. The noise present in the received speech signal presents significant qualitative and functional problems for a variety of downstream speech processing applications of the host communication device, applications including basic voice services and speech recognition for example.

Another device used for detecting speech is a physiological microphone, also referred to as a "P-Mic". The P-Mic detects body vibrations generated during speech through the use of a small gel-filled cushion coupled to a piezo-sensor. Since the gel cushion couples well to the human flesh and poorly to the air, the P-Mic can accurately detect speech vibrations when placed against the skin, even in high noise environments. However, this solution requires firm contact between the gel cushion and the skin to work effectively—a requirement the consumer market is unlikely to accept. Further, at a size of approximately 1.5 inches on a side, the P-Mic is typically too large for deployment into many consumer communication products. Additionally, the P-Mic is prohibitively expensive to see widespread use in consumer products such as headsets. Also, the P-Mic does not use a standard microphone electrical interface so additional circuitry is required in order to connect the P-Mic to an analog-to-digital converter, increasing both size and implementation cost.

Yet another common device typically used for detecting speech, which is similar in principle to the P-Mic, is a Bone Conduction Microphone (BCM). The BCM includes an accelerometer used to measure skin/flesh vibrations generated by speech. The accelerometer of the BCM measures its own displacement caused by speech vibrations. However, much like the P-Mic, accelerometers require good contact to work effectively and are currently too expensive and electronically cumbersome to be used in commercial communications products. Again, accelerometers cannot use a standard microphone electrical interface so additional circuitry is required to connect the accelerometer to an analog-to-digital converter, thereby increasing both size and implementation cost.

Figure 1:
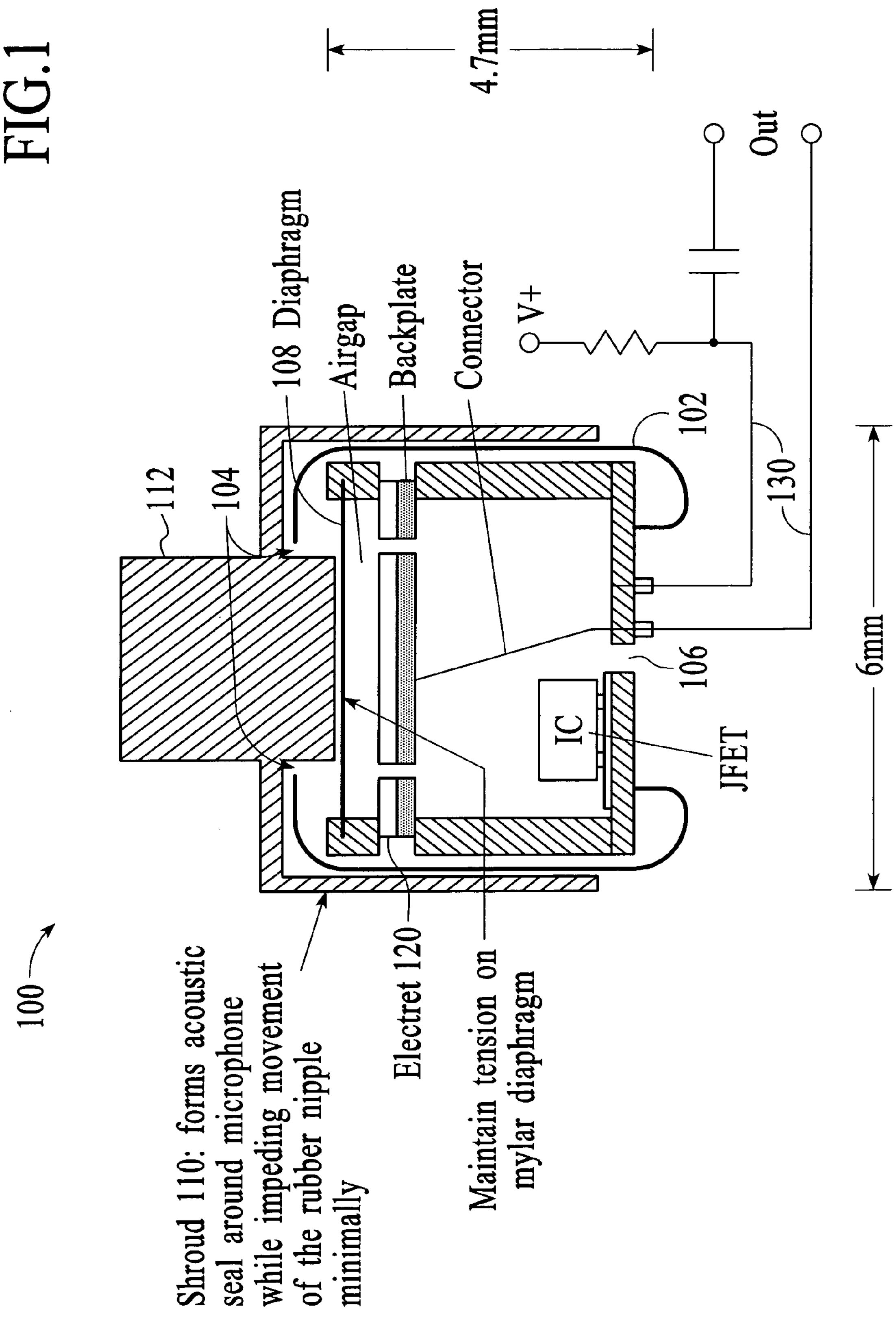
FIG. 1 is a cross section view of an acoustic vibration sensor, under an embodiment.

In the drawings, the same reference numbers identify identical or substantially similar elements or acts. To easily identify the discussion of any particular element or act, the most significant digit or digits in a reference number refer to the Figure number in which that element is first introduced (e.g., element 100 is first introduced and discussed with respect to FIG. 1).

DETAILED DESCRIPTION

An acoustic vibration sensor, also referred to as a speech sensing device, is described below. The acoustic vibration sensor is similar to a microphone in that it captures speech information from the head area of a human talker or talker in noisy environments. This information can then be used to generate a Voice Activity Detection (VAD) Signal, which is useful in many speech applications. Previous solutions to this problem have either been vulnerable to noise, physically too large for certain applications, or cost prohibitive. In contrast, the acoustic vibration sensor described herein accurately detects and captures speech vibrations in the presence of substantial airborne acoustic noise, yet within a smaller and less expensive physical package. The noise-resistant speech information provided by the acoustic vibration sensor can subsequently be used in downstream speech processing applications (speech enhancement and noise suppression, speech encoding, speech recognition, talker verification, etc.) to improve the performance of those applications.

The following description provides specific details for a thorough understanding of, and enabling description for, embodiments of a transducer. However, one skilled in the art will understand that the invention may be practiced without these details. In other instances, well-known structures and functions have not been shown or described in detail to avoid unnecessarily obscuring the description of the embodiments of the invention.

Figure 2A:
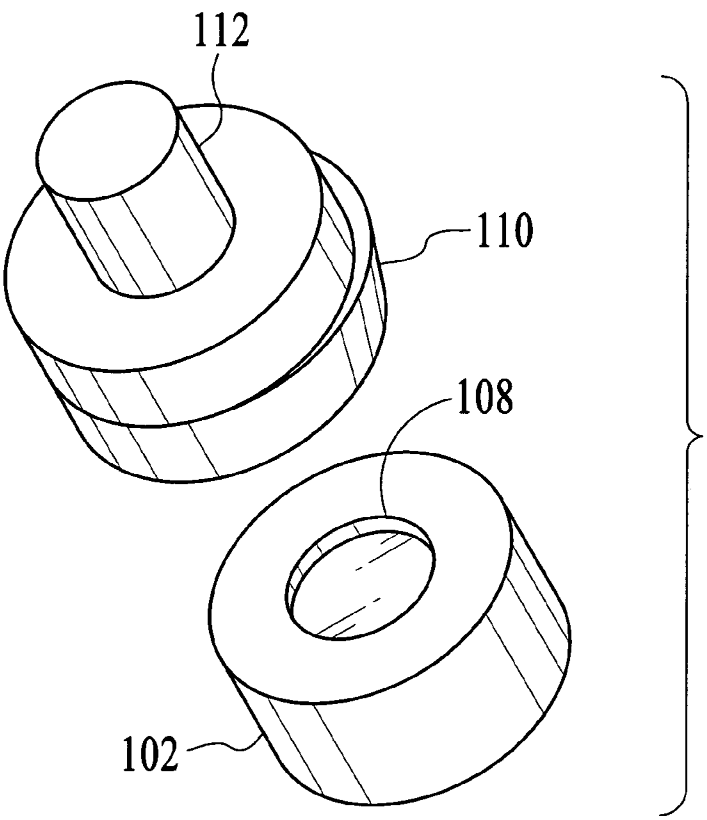
FIG. 2A is an exploded view of an acoustic vibration sensor, under the embodiment of FIG. 1.
Figure 2B:
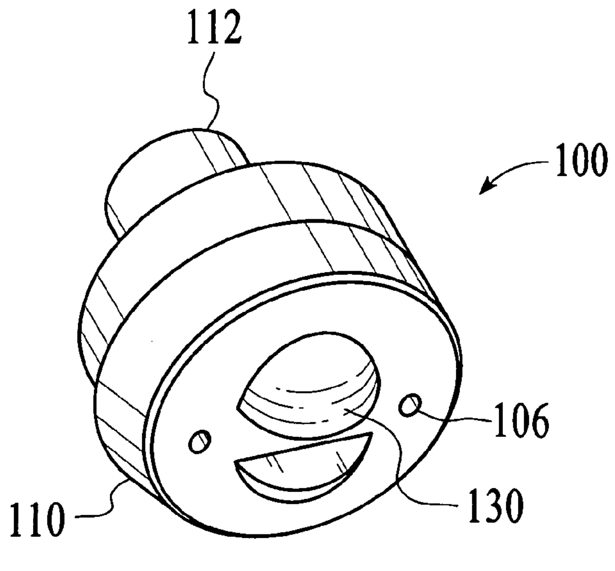
FIG. 2B is perspective view of an acoustic vibration sensor, under the embodiment of FIG. 1.

FIG. 1 is a cross section view of an acoustic vibration sensor 100, also referred to herein as the sensor 100, under an embodiment. FIG. 2A is an exploded view of an acoustic vibration sensor 100, under the embodiment of FIG. 1. FIG. 2B is perspective view of an acoustic vibration sensor 100, under the embodiment of FIG. 1. The sensor 100 includes an enclosure 102 having a first port 104 on a first side and at least one second port 106 on a second side of the enclosure 102. A diaphragm 108, also referred to as a sensing diaphragm 108, is positioned between the first and second ports. A coupler 110, also referred to as the shroud 110 or cap 110, forms an acoustic seal around the enclosure 102 so that the first port 104 and the side of the diaphragm facing the first port 104 are isolated from the airborne acoustic environment of the human talker. The coupler 110 of an embodiment is contiguous, but is not so limited. The second port 106 couples a second side of the diaphragm to the external environment.

The sensor also includes electret microphone 120 and the associated components and electronics coupled to receive acoustic signals from the talker via the coupler 110 and the diaphragm 108 and convert the acoustic signals to electrical signals representative of human speech. Electrical contacts 130 provide the electrical signals as an output. Alternative embodiments can use any type/combination of materials and/or electronics to convert the acoustic signals to electrical signals representative of human speech and output the electrical signals.

The coupler 110 of an embodiment is formed using materials having acoustic impedances matched to the impedance of human skin (characteristic acoustic impedance of skin is approximately $1.5\times10^6$ Pa×s/m). The coupler 110 therefore, is formed using a material that includes at least one of silicone gel, dielectric gel, thermoplastic elastomers (TPE), and rubber compounds, but is not so limited. As an example, the coupler 110 of an embodiment is formed using Kraiburg TPE products. As another example, the coupler 110 of an embodiment is formed using Sylgard® Silicone products.

The coupler 110 of an embodiment includes a contact device 112 that includes, for example, a nipple or protrusion that protrudes from either or both sides of the coupler 110. In operation, a contact device 112 that protrudes from both sides of the coupler 110 includes one side of the contact device 112 that is in contact with the skin surface of the talker and another side of the contact device 112 that is in contact with the diaphragm, but the embodiment is not so limited. The coupler 110 and the contact device 112 can be formed from the same or different materials.

The coupler 110 transfers acoustic energy efficiently from skin/flesh of a talker to the diaphragm, and seals the diaphragm from ambient airborne acoustic signals. Consequently, the coupler 110 with the contact device 112 efficiently transfers acoustic signals directly from the talker's body (speech vibrations) to the diaphragm while isolating the diaphragm from acoustic signals in the airborne environment of the talker (characteristic acoustic impedance of air is approximately 415 Pa×s/m). The diaphragm is isolated from acoustic signals in the airborne environment of the talker by the coupler 110 because the coupler 110 prevents the signals from reaching the diaphragm, thereby reflecting and/or dissipating much of the energy of the acoustic signals in the airborne environment. Consequently, the sensor 100 responds primarily to acoustic energy transferred from the skin of the talker, not air. When placed against the head of the talker, the sensor 100 picks up speech-induced acoustic signals on the surface of the skin while airborne acoustic noise signals are largely rejected, thereby increasing the signal-to-noise ratio and providing a very reliable source of speech information.

Performance of the sensor 100 is enhanced through the use of the seal provided between the diaphragm and the airborne environment of the talker. The seal is provided by the coupler 110. A modified gradient microphone is used in an embodiment because it has pressure ports on both ends. Thus, when the first port 104 is sealed by the coupler 110, the second port 106 provides a vent for air movement through the sensor 100.

Figure 3:
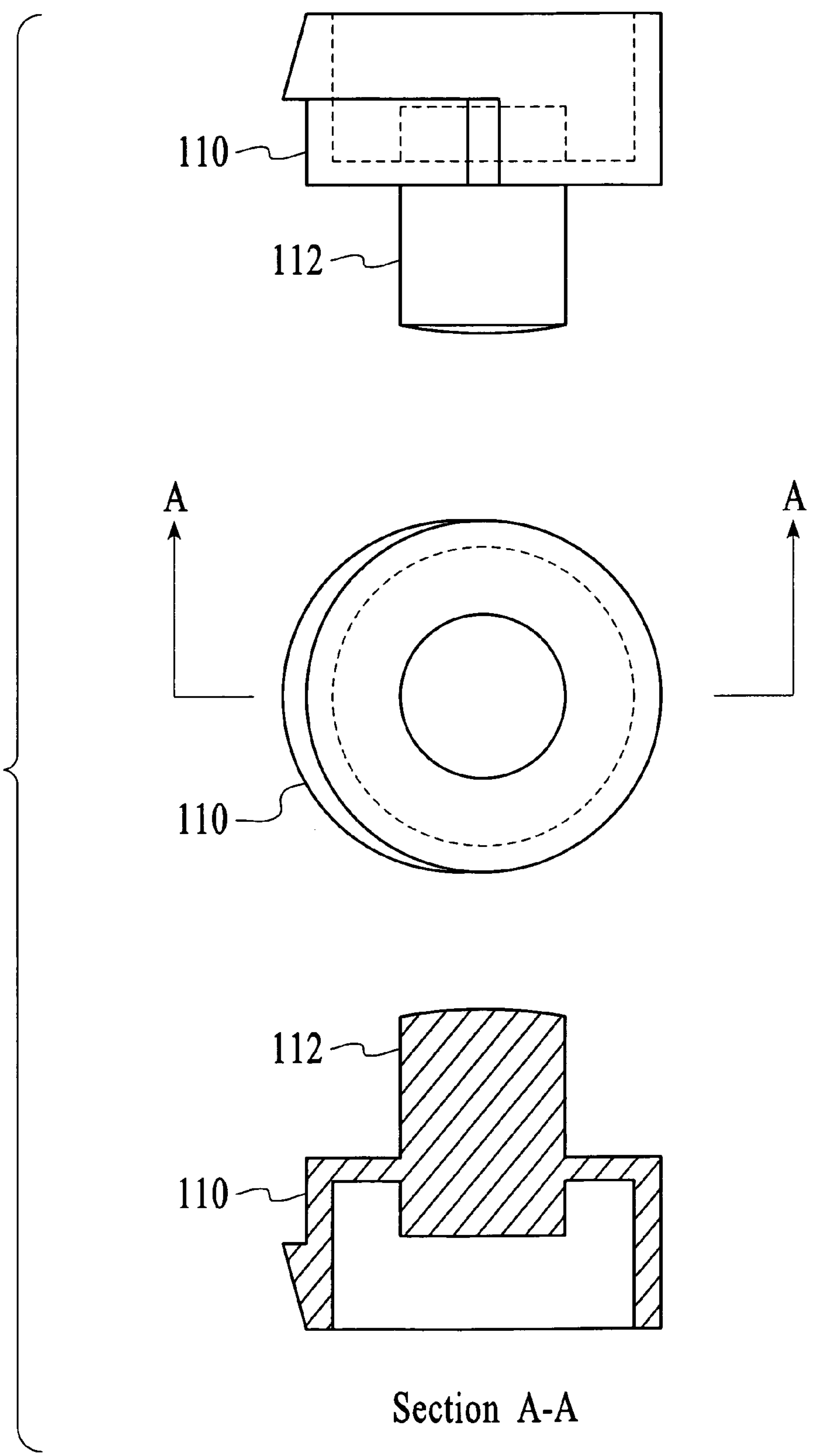
FIG. 3 is a schematic diagram of a coupler of an acoustic vibration sensor, under the embodiment of FIG. 1.

FIG. 3 is a schematic diagram of a coupler 110 of an acoustic vibration sensor, under the embodiment of FIG. 1. The dimensions shown are in millimeters and are only intended to serve as an example for one embodiment. Alternative embodiments of the coupler can have different configurations and/or dimensions. The dimensions of the coupler 110 show that the acoustic vibration sensor 100 is small in that the sensor 100 of an embodiment is approximately the same size as typical microphone capsules found in mobile communication devices. This small form factor allows for use of the sensor 110 in highly mobile miniaturized applications, where some example applications include at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

The acoustic vibration sensor provides very accurate Voice Activity Detection (VAD) in high noise environments, where high noise environments include airborne acoustic environments in which the noise amplitude is as large if not larger than the speech amplitude as would be measured by conventional omnidirectional microphones. Accurate VAD information provides significant performance and efficiency benefits in a number of important speech processing applications including but not limited to: noise suppression algorithms such as the Pathfinder algorithm available from Aliph, Brisbane, Calif. and described in the Related Applications; speech compression algorithms such as the Enhanced Variable Rate Coder (EVRC) deployed in many commercial systems; and speech recognition systems.

In addition to providing signals having an improved signal-to-noise ratio, the acoustic vibration sensor uses only minimal power to operate (on the order of 200 micro Amps, for example). In contrast to alternative solutions that require power, filtering, and/or significant amplification, the acoustic vibration sensor uses a standard microphone interface to connect with signal processing devices. The use of the standard microphone interface avoids the additional expense and size of interface circuitry in a host device and supports for of the sensor in highly mobile applications where power usage is an issue.

Figure 4:
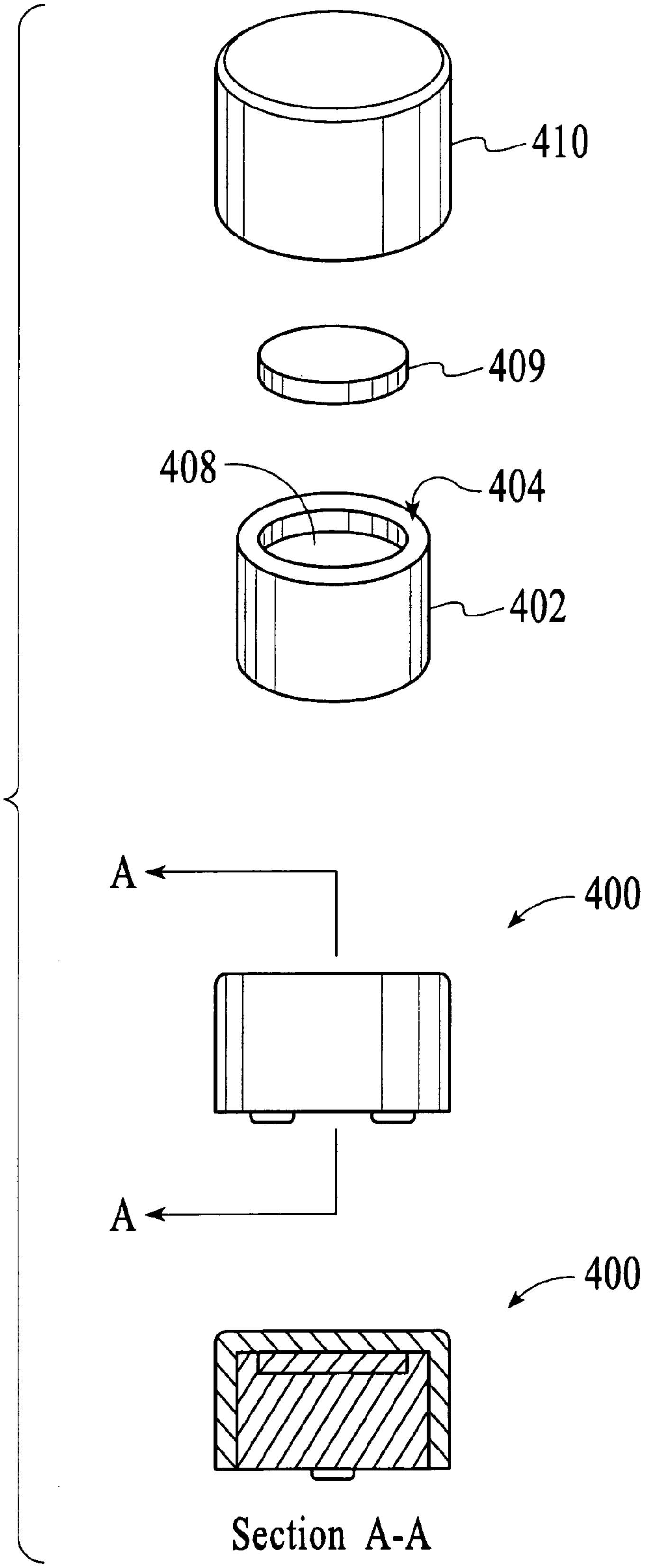
FIG. 4 is an exploded view of an acoustic vibration sensor, under an alternative embodiment.

FIG. 4 is an exploded view of an acoustic vibration sensor 400, under an alternative embodiment. The sensor 400 includes an enclosure 402 having a first port 404 on a first side and at least one second port (not shown) on a second side of the enclosure 402. A diaphragm 408 is positioned between the first and second ports. A layer of silicone gel 409 or other similar substance is formed in contact with at least a portion of the diaphragm 408. A coupler 410 or shroud 410 is formed around the enclosure 402 and the silicon gel 409 where a portion of the coupler 410 is in contact with the silicon gel 409. The coupler 410 and silicon gel 409 in combination form an acoustic seal around the enclosure 402 so that the first port 404 and the side of the diaphragm facing the first port 404 are isolated from the acoustic environment of the human talker. The second port couples a second side of the diaphragm to the acoustic environment.

As described above, the sensor includes additional electronic materials as appropriate that couple to receive acoustic signals from the talker via the coupler 410, the silicon gel 409, and the diaphragm 408 and convert the acoustic signals to electrical signals representative of human speech. Alternative embodiments can use any type/combination of materials and/or electronics to convert the acoustic signals to electrical signals representative of human speech.

The coupler 410 and/or gel 409 of an embodiment are formed using materials having impedances matched to the impedance of human skin. As such, the coupler 410 is formed using a material that includes at least one of silicone gel, dielectric gel, thermoplastic elastomers (TPE), and rubber compounds, but is not so limited. The coupler 410 transfers acoustic energy efficiently from skin/flesh of a talker to the diaphragm, and seals the diaphragm from ambient airborne acoustic signals. Consequently, the coupler 410 efficiently transfers acoustic signals directly from the talker's body (speech vibrations) to the diaphragm while isolating the diaphragm from acoustic signals in the airborne environment of the talker. The diaphragm is isolated from acoustic signals in the airborne environment of the talker by the silicon gel 409/coupler 410 because the silicon gel 409/coupler 410 prevents the signals from reaching the diaphragm, thereby reflecting and/or dissipating much of the energy of the acoustic signals in the airborne environment. Consequently, the sensor 400 responds primarily to acoustic energy transferred from the skin of the talker, not air. When placed again the head of the talker, the sensor 400 picks up speech-induced acoustic signals on the surface of the skin while airborne acoustic noise signals are largely rejected, thereby increasing the signal-to-noise ratio and providing a very reliable source of speech information.

Figure 5:
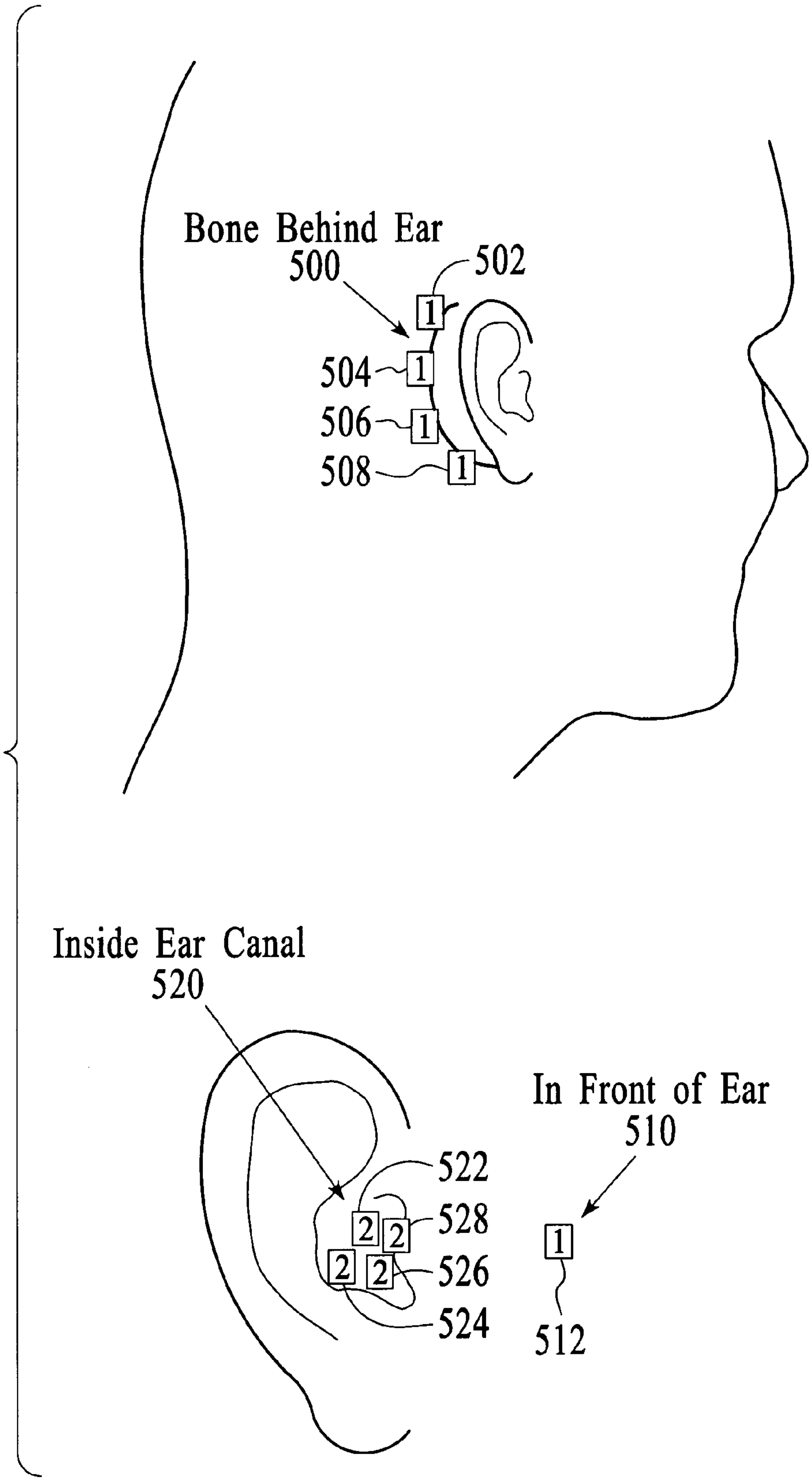
FIG. 5 shows representative areas of sensitivity on the human head appropriate for placement of the acoustic vibration sensor, under an embodiment.

There are many locations outside the ear from which the acoustic vibration sensor can detect skin vibrations associated with the production of speech. The sensor can be mounted in a device, handset, or earpiece in any manner, the only restriction being that reliable skin contact is used to detect the skin-borne vibrations associated with the production of speech. FIG. 5 shows representative areas of sensitivity 500-520 on the human head appropriate for placement of the acoustic vibration sensor 100/400, under an embodiment. The areas of sensitivity 500-520 include numerous locations 502-508 in an area behind the ear 500, at least one location 512 in an area in front of the ear 510, and in numerous locations 522-528 in the ear canal area 520. The areas of sensitivity 500-520 are the same for both sides of the human head. These representative areas of sensitivity 500-520 are provided as examples only and do not limit the embodiments described herein to use in these areas.

Figure 6:
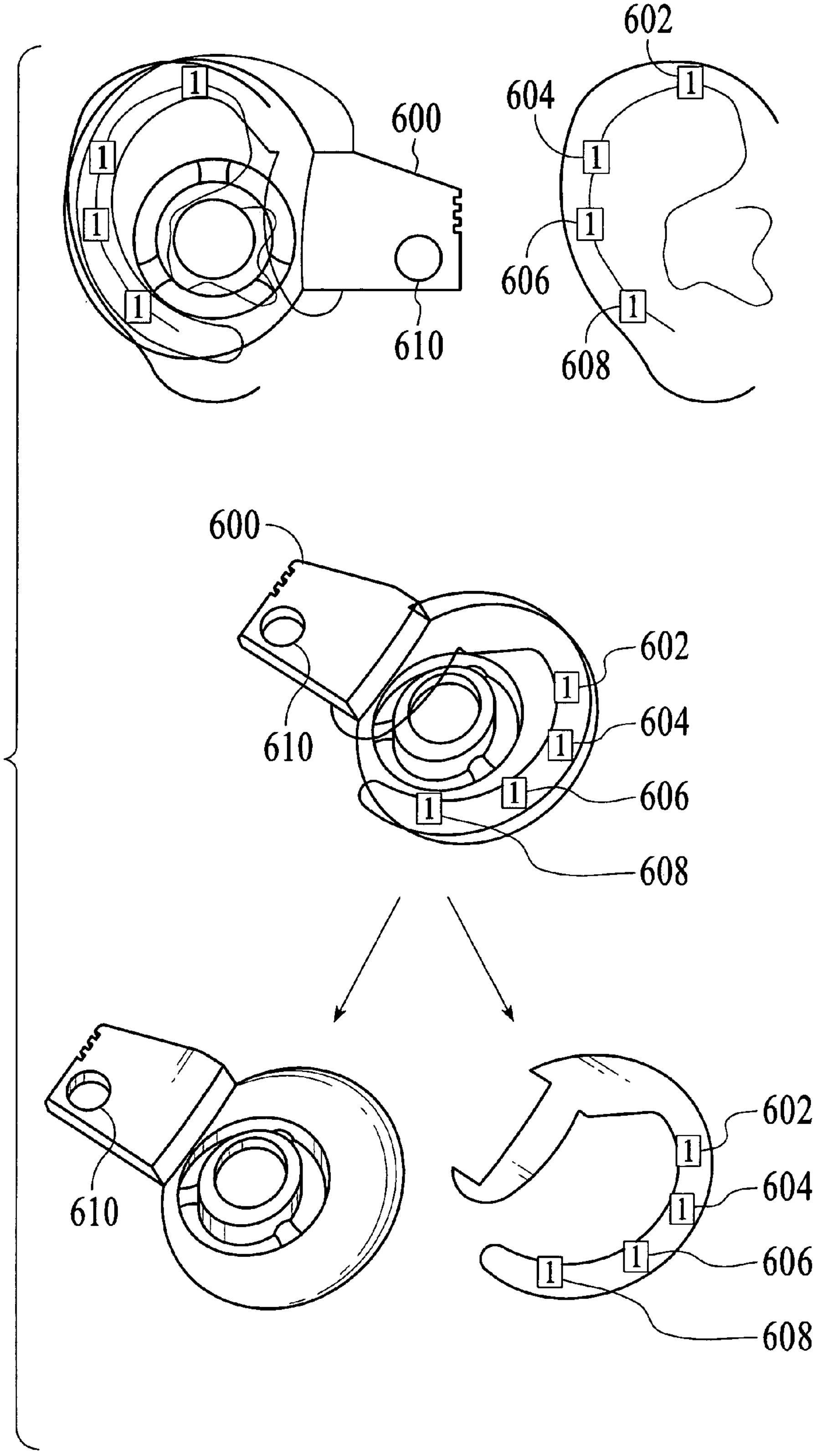
FIG. 6 is a generic headset device that includes an acoustic vibration sensor placed at any of a number of locations, under an embodiment.

FIG. 6 is a generic headset device 600 that includes an acoustic vibration sensor 100/400 placed at any of a number of locations 602-610, under an embodiment. Generally, placement of the acoustic vibration sensor 100/400 can be on any part of the device 600 that corresponds to the areas of sensitivity 500-520 (FIG. 5) on the human head. While a headset device is shown as an example, any number of communication devices known in the art can carry and/or couple to an acoustic vibration sensor 100/400.

Figure 7:
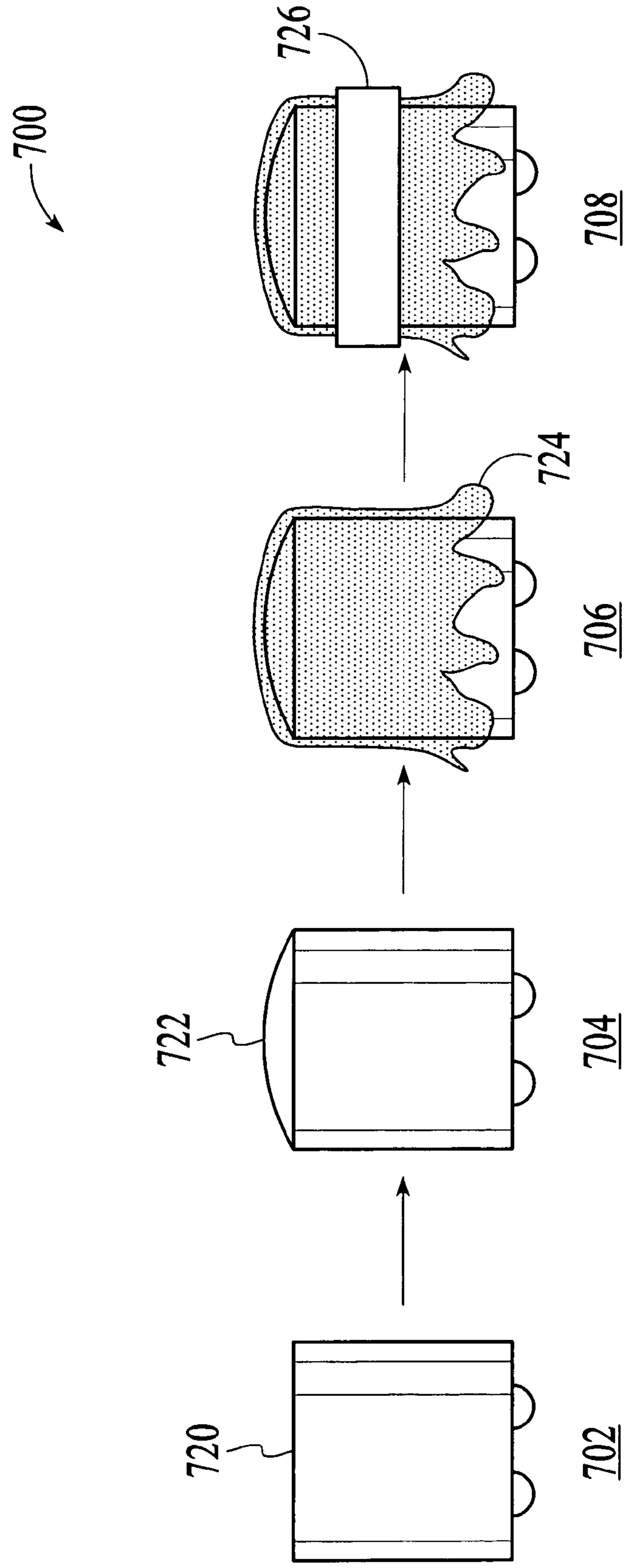
FIG. 7 is a diagram of a manufacturing method for an acoustic vibration sensor, under an embodiment.

FIG. 7 is a diagram of a manufacturing method 700 for an acoustic vibration sensor, under an embodiment. Operation begins with, for example, a uni-directional microphone 720, at block 702. Silicon gel 722 is formed over/on the diaphragm (not shown) and the associated port, at block 704. A material 724, for example polyurethane film, is formed or placed over the microphone 720/silicone gel 722 combination, at block 706, to form a coupler or shroud. A snug fit collar or other device is placed on the microphone to secure the material of the coupler during curing, at block 708.

Note that the silicon gel (block 702) is an optional component that depends on the embodiment of the sensor being manufactured, as described above. Consequently, the manufacture of an acoustic vibration sensor 100 that includes a contact device 112 (referring to FIG. 1) will not include the formation of silicon gel 722 over/on the diaphragm. Further, the coupler formed over the microphone for this sensor 100 will include the contact device 112 or formation of the contact device 112.

An acoustic vibration sensor, also referred to as a speech sensing device or sensor, is provided. The sensor, which generates electrical signals, comprises: at least one diaphragm positioned adjacent a front port; and at least one coupler configured to couple a first set of signals to the diaphragm and reject a second set of signals by isolating the diaphragm from the second set of signals, wherein the coupler includes at least one material having an acoustic impedance matched to an impedance of human skin.

The coupler of an embodiment couples to skin of a human talker and the first set of signals include speech signals of the talker and the second set of signals include noise of an airborne acoustic environment of the talker.

The coupler of an embodiment includes a first protrusion on a first side of the coupler that contacts a surface of the human skin and a second protrusion on a second side of the coupler that contacts the diaphragm.

The sensor of an embodiment includes a coupler having a first side that contacts the human skin and a second side that couples to the diaphragm via at least one layer of gel material.

The coupler of an embodiment comprises at least one material including at least one of silicone gel, dielectric gel, thermoplastic elastomers (TPE), and rubber compounds.

An acoustic sensor is provided that comprises: a first port on a first side of an enclosure; a second port on a second side of an enclosure; at least one diaphragm positioned between the first and second ports; and a contiguous coupler having a first portion that couples a first side of the diaphragm to skin of a human talker and a second portion that isolates the first side of the diaphragm from an acoustic environment of the human talker, wherein the coupler includes at least one material having an acoustic impedance matched to the impedance of skin.

The sensor of an embodiment further comprises an electret microphone coupled to receive acoustic signals from the talker via the coupler and the diaphragm, wherein the electret microphone is used to convert the acoustic signals to electrical signals.

The coupler of an embodiment comprises at least one material including at least one of silicone gel, dielectric gel, thermoplastic elastomers (TPE), and rubber compounds.

The coupler of an embodiment includes a contact device comprising a first side that contacts the skin and a second side that contacts the diaphragm.

In the sensor of an embodiment the second port couples a second side of the diaphragm to the airborne acoustic environment.

A communication system is provided that comprises: at least one signal processor; and at least one acoustic sensor that couples electrical signals representative of human speech to the signal processor, the sensor including at least one diaphragm positioned between a first port and a second port of an enclosure, the sensor further including a contiguous coupler comprising at least one material having an acoustic impedance matched to the impedance of skin, wherein the coupler includes a first portion that couples a first side of the diaphragm to skin of a human talker and a second portion that isolates a first side of the diaphragm from an acoustic environment of the human talker.

The communication system of an embodiment further comprises a portable communication device that includes the acoustic sensor, wherein the portable communication device includes at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

A device for sensing speech signals is provided that comprises means for receiving speech signals, along with means for coupling a first set of signals to the means for receiving and rejecting a second set of signals, wherein the means for coupling isolates the means for receiving from the second set of signals, wherein the means for coupling includes at least one material having an impedance matched to an impedance of human skin.

Aspects of the acoustic vibration sensor described herein may be implemented using any of a variety of materials and methods. Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the acoustic vibration sensor is not intended to be exhaustive or to limit the system to the precise form disclosed. While specific embodiments of, and examples for, the acoustic vibration sensor are described herein for illustrative purposes, various equivalent modifications are possible within the scope of the sensor, as those skilled in the relevant art will recognize. The teachings of the acoustic vibration sensor provided herein can be applied to other sensing devices and systems, not only for the sensors described above.

The elements and acts of the various embodiments described above can be combined to provide further embodiments. These and other changes can be made to the acoustic vibration sensor in light of the above detailed description.

All of the above references and United States patents and patent applications are incorporated herein by reference. Aspects of the acoustic vibration sensor can be modified, if necessary, to employ the systems, functions and concepts of the various patents and applications described above to provide yet further embodiments of the acoustic vibration sensor.

In general, in the following claims, the terms used should not be construed to limit the acoustic vibration sensor to the specific embodiments disclosed in the specification and the claims, but should be construed to include all sensors and speech processing systems that operate under the claims to provide sensing capabilities. Accordingly, the acoustic vibration sensor is not limited by the disclosure, but instead the scope of the sensor is to be determined entirely by the claims.

While certain aspects of the acoustic vibration sensor are presented below in certain claim forms, the inventors contemplate the various aspects of the sensor in any number of claim forms. Accordingly, the inventors reserve the right to add additional claims after filing the application to pursue such additional claim forms for other aspects of the acoustic vibration sensor.

We claim:

1. A sensor for generating electrical signals, comprising:

a diaphragm positioned adjacent a front port and a rear port; and a coupler configured to couple a first set of signals to a first side of the diaphragm and reject a second set of signals by isolating the diaphragm from the second set of signals, wherein the coupler includes a protrusion on a first side of the coupler that couples to the first side of the diaphragm, wherein the rear port couples a second side of the diaphragm to an airborne acoustic environment of a human talker.

2. The sensor of claim 1, wherein the coupler is coupled to skin of the human talker and the first set of signals include speech signals of the human talker and the second set of signals include noise of the airborne acoustic environment of the human talker.

3. The sensor of claim 1, wherein the coupler includes a protrusion on a second side of the coupler that contacts a surface of the human skin.

4. The sensor of claim 1, wherein a second side of the coupler contacts the human skin and the first side of the coupler couples to the diaphragm via at least one layer of a material comprising gel material.

5. The sensor of claim 1, wherein the coupler comprises at least one material including at least one of silicone gel, dielectric gel, thermoplastic elastomers (TPE), and rubber compounds.

6. The sensor of claim 1, further comprising an electret microphone coupled to receive acoustic signals from the talker via the coupler and the diaphragm, wherein the electret microphone is used to convert the acoustic signals to the electrical signals.

7. An acoustic sensor, comprising:

a first port on a first side of an enclosure;

a second port on a second side of an enclosure;

a diaphragm positioned between the first and second ports; and a contiguous coupler having a first portion that couples a first side of the diaphragm to skin of a human talker, a second portion that couples to the diaphragm, and a third portion that isolates the first side of the diaphragm from an airborne acoustic environment of the human talker;

wherein the second port couples a second side of the diaphragm to the airborne acoustic environment.

8. The sensor of claim 7, further comprising an electret microphone coupled to receive acoustic signals from the talker via the coupler and the diaphragm, wherein the electret microphone is used to convert the acoustic signals to electrical signals.

9. The sensor of claim 7, wherein the coupler comprises at least one material including at least one of silicone gel, dielectric gel, thermoplastic elastomers (TPE), and rubber compounds.

10. A communication system, comprising:

at least one signal processor; and at least one acoustic sensor that couples electrical signals representative of human speech to the signal processor, the sensor including a diaphragm positioned behind a first port of an enclosure and a contiguous coupler, wherein the contiguous coupler comprises, a first portion that couples to the diaphragm;

a second portion that contacts skin of a human talker; and a portion that isolates a first side of the diaphragm from an airborne acoustic environment of the human talker, wherein a second port couples a second side of the diaphragm to the airborne acoustic environment.

11. The system of claim 10, further including a portable communication device that includes the acoustic sensor, wherein the portable communication device includes at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

12. A Voice Activity Detector (VAD) sensor for generating an electrical VAD signal, comprising:

a diaphragm positioned adjacent a front port and a rear port; and a coupler configured to couple a first set of signals to a first side of the diaphragm and reject a second set of signals by isolating the diaphragm from the second set of signals, wherein the coupler includes a protrusion on a first side of the coupler that couples to the first side the diaphragm, wherein the rear port couples a second side of the diaphragm to an airborne acoustic environment of a human talker.

13. The VAD sensor of claim 12, wherein the coupler is coupled to skin of the human talker and the first set of signals includes speech signals of the human talker and the second set of signals include noise of the airborne acoustic environment of the human talker.

14. The VAD sensor of claim 12, wherein the coupler includes a protrusion on a second side of the coupler that contacts a surface of the human skin.

15. The VAD sensor of claim 12, wherein a second side of the coupler contacts the human skin and the first side of the coupler couples to the diaphragm via at least one layer of a material comprising gel material.

16. The sensor of claim 12, wherein the coupler comprises at least one material including at least one of silicone gel, dielectric gel, thermoplastic elastomers (TPE), and rubber compounds.

17. The sensor of claim 12, further comprising an electret microphone coupled to receive acoustic signals from the talker via the coupler and the diaphragm, wherein the electret microphone is used to convert the acoustic signals to the electrical signals.

* * * * *